United States Patent [19]
Thorne et al.

[11] Patent Number: 5,144,151
[45] Date of Patent: Sep. 1, 1992

[54] APPARATUS AND METHOD FOR DETECTING THE PRESENCE OF A DISCONTINUITY ON A GLASS SURFACE

[76] Inventors: Brent a. Thorne, 6519 Heritage, West Bloomfield, Mich. 48332; Salvatore J. Riera, 61801 Cetnor, Washington, Mich. 48094

[21] Appl. No.: 672,173

[22] Filed: Mar. 20, 1991

[51] Int. Cl.[5] ............................................. G01N 21/86
[52] U.S. Cl. ....................................... 250/571; 356/445
[58] Field of Search .................. 250/571, 572; 356/445

[56] References Cited

U.S. PATENT DOCUMENTS

| | | | |
|---|---|---|---|
| 3,807,870 | 4/1974 | Kalman | 250/571 |
| 3,892,492 | 7/1975 | Eichenberger | 250/571 |
| 3,906,232 | 9/1975 | Meihofer | 250/571 |
| 4,044,250 | 8/1977 | Fetzer | 250/571 |
| 4,091,368 | 5/1978 | Schwartz | 250/571 |
| 4,139,307 | 2/1979 | Clarke | 250/571 |
| 4,754,148 | 6/1988 | Barkowski et al. | 250/571 |
| 4,857,749 | 8/1989 | McCarty | 250/571 |

Primary Examiner—Janice A. Howell
Assistant Examiner—Kiet T. Nguyen
Attorney, Agent, or Firm—Brooks & Kushman

[57] ABSTRACT

The present invention is directed to an apparatus and method for detecting the presence or absence of a discontinuity on a glass surface. The apparatus includes a transmitting means for directing and receiving infrared electromagnetic radiation relative to the glass surface, a positioning means for positioning the transmitting means in a fixed angular and distance relation with respect to the glass surface, and a sensing means for determining the relative magnitude of the received radiation, the magnitude being indicative of the presence or absence of a discontinuity. The apparatus may be translated relative to the glass surface to detect discontinuities therealong.

14 Claims, 2 Drawing Sheets

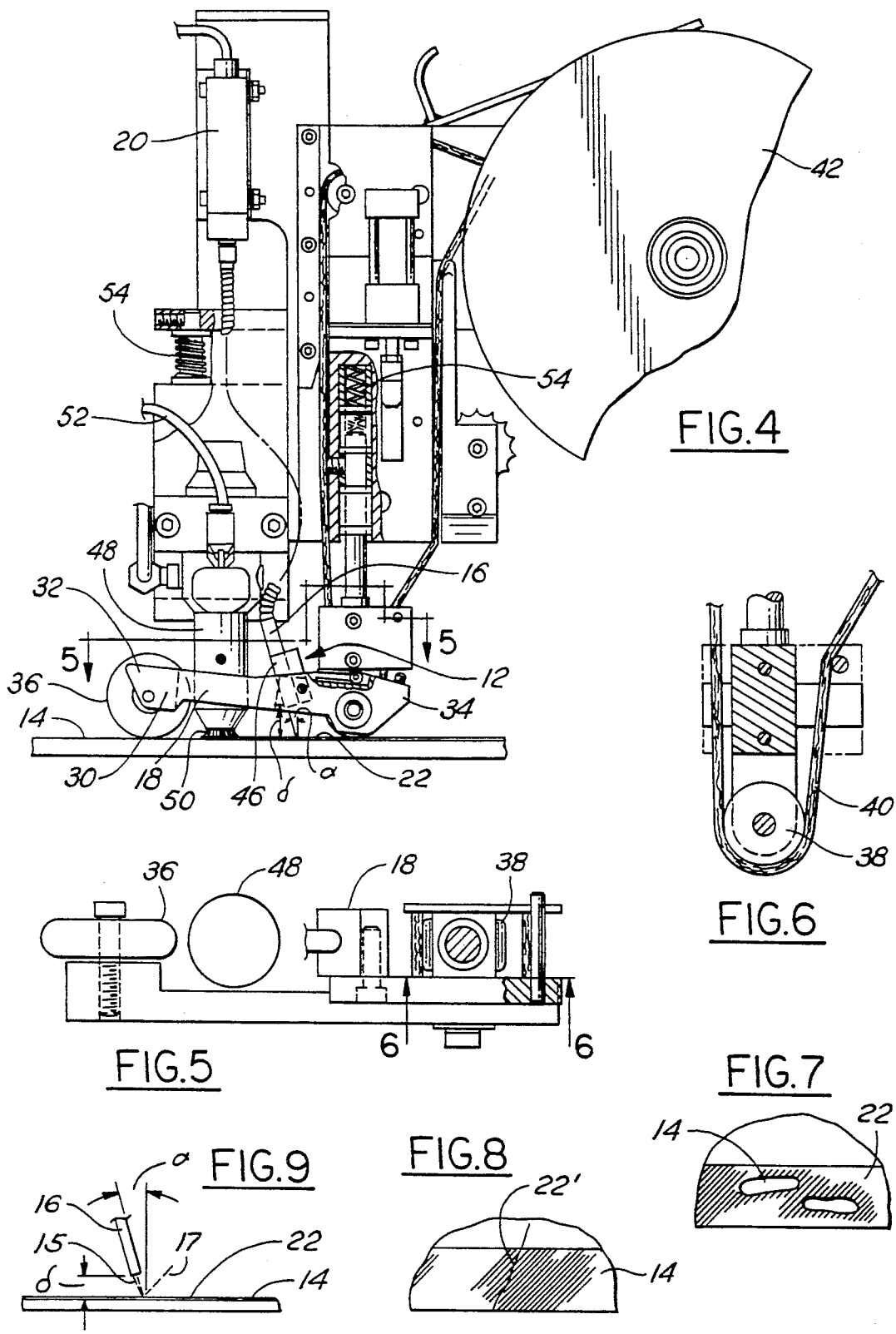

APPARATUS AND METHOD FOR DETECTING THE PRESENCE OF A DISCONTINUITY ON A GLASS SURFACE

TECHNICAL FIELD

This invention relates generally to an apparatus and method for detecting the presence or absence of a discontinuity on a glass surface, and in particular an apparatus or method using a photoelectric sensor.

BACKGROUND ART

Automotive glass sheets such as front windows or back lights are generally adhesively secured within window frames of automotive vehicles. Prior to installation, a number of preparation steps are required to insure that the adhesive properly secures the glass within the frame.

The first step is to chemically etch the marginal edge of the glass. This is accomplished by the application of a liquid primer which etches and cleans the glass surface. After applying this solution by brush, dobbing, spraying or other means, this primer is wiped away with a lint free substance to provide a clear, dry surface.

The second step is to apply a black primer to the etched edge of the glass prior to the application of a urethane sealant. The black primer protects the urethane sealant from sunlight which causes deterioration in the sealant. The black primer is applied by means of a brush, spray or drip and is allowed to dry. Then the urethane sealant is applied prior to installation of the glass in the vehicle.

A serious problem over the years has been to detect whether the primers, in particular the etching primer which is generally clear, ave been applied continuously along the marginal edges of the glass surface. If any primer, either the etching primer or the black primer, is not applied, the bonding of the urethane sealant may fail resulting in the glass coming free of the automotive vehicle.

Various approaches, i.e., camera systems, thermal sensors, and flow sensors have been experimented with and capacitative probes have been inserted into a brush applying the primers all in an effort to determine whether the sealant has been or is being applied to the glass. None of these approaches has proven satisfactory.

These means of detection of the primer coatings suffer from several disadvantages. First, typically a rather large quantity of primer must be present in order for these detection means to insure detection of their presence. A second problem is that these detection means generally indicate only whether a coating is present and do not readily quantify the amount present. Third, these means are not suitable to sense the presence of a coating on a glass surface as the sensing means moves relative to the glass surface.

Previous attempts at directing electromagnetic radiation perpendicularly downward towards a glass surface and measuring the difference between the reflectivity of a wet surface and a dry surface has proven unsuccessful in determining the presence or absence of a coating of primer.

DISCLOSURE OF INVENTION

It has been discovered that there exists a difference in the relative reflectivity of incident infrared electromagnetic radiation upon a dry versus wet glass surface when the incident radiation is directed at an angle of 3°–18° from a line perpendicular to the glass surface. The present invention senses this difference in reflectivity to determine the presence or absence of liquid coating on a glass surface. Further, this invention may detect the presence of a crack on a glass surface due to the change in reflectivity of incident radiation upon the glass surface with a crack therein.

The present invention includes an apparatus for detecting the presence or absence of a discontinuity on a glass surface. These discontinuities include a coating such a liquid primer or a crack located on a glass surface. The apparatus comprises a transmitting means for directing electromagnetic radiation in the infrared range toward a glass surface and for receiving infrared electromagnetic radiation reflected back from the glass surface. Also included is a sensing means for sensing the relative strength of the reflected radiation to determine the presence or absence of a discontinuity. The invention further includes a positioning means for positioning the transmitting means in a fixed angular and distance relation relative to the glass surface. The apparatus may be moved relative to the glass surface to sense the presence of a discontinuity over a continuous region of the glass surface.

The present invention has several advantages over other detection apparatus and methods. First, the present invention is more sensitive to discontinuities than the apparatus and methods used in the past. Second, the present invention can be used to evaluate the presence of a discontinuity as the apparatus moves relative to the glass surface at a relatively high rate of speed. Finally, this invention can, to a degree, quantify the amount of material present on a glass surface.

An important object of the present invention is to overcome the disadvantages and problems encountered with respect to prior methods of detecting discontinuities on a glass surface and in particular to detecting coatings on the surface.

Another object is to provide a more sensitive method for detecting the presence or lack of presence of a discontinuity on a glass surface as compared to prior methods used.

Yet another object is to provide an apparatus and a method wherein the sensing of a discontinuity as the sensing device moves relative to a glass surface is performed at a relatively high rate of speed.

Other objects, features and advantages will become more readily apparent from the following description and accompanying sheet of drawings.

BRIEF DESCRIPTION OF THE DRAWINGS

FIG. 4 is a partial side view of the apparatus engaging the glass surface;

FIG. 5 is a top sectional view taken along line 5—5 of FIG. 4;

FIG. 6 is a partial side view taken along line 6—6 of FIG. 5 showing a felt ribbon which removes a coating residing on the glass surface;

FIG. 7 is a top view of a coating of primer on a glass surface with patches of primer missing;

FIG. 8 is a top view of a glass surface having a crack located therein which may be detected by the apparatus or method of the present invention; and FIG. 9 is a partial side view schematically showing radiation emitted by a transmitting means directed upon and partially reflecting back to the transmitting means.

BEST MODE FOR CARRYING OUT THE INVENTION

Figure 1:
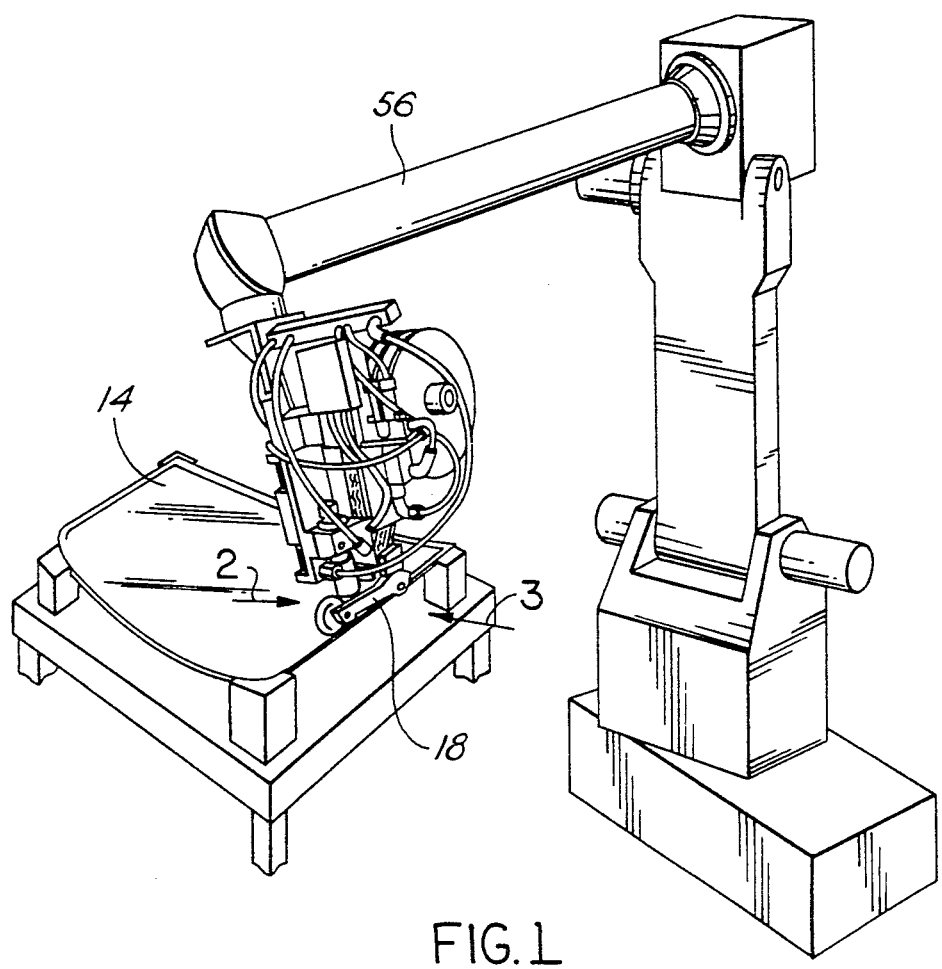
FIG. 1 is perspective view of an apparatus made in accordance with the present invention being translated relative to a glass surface.
Figure 2:
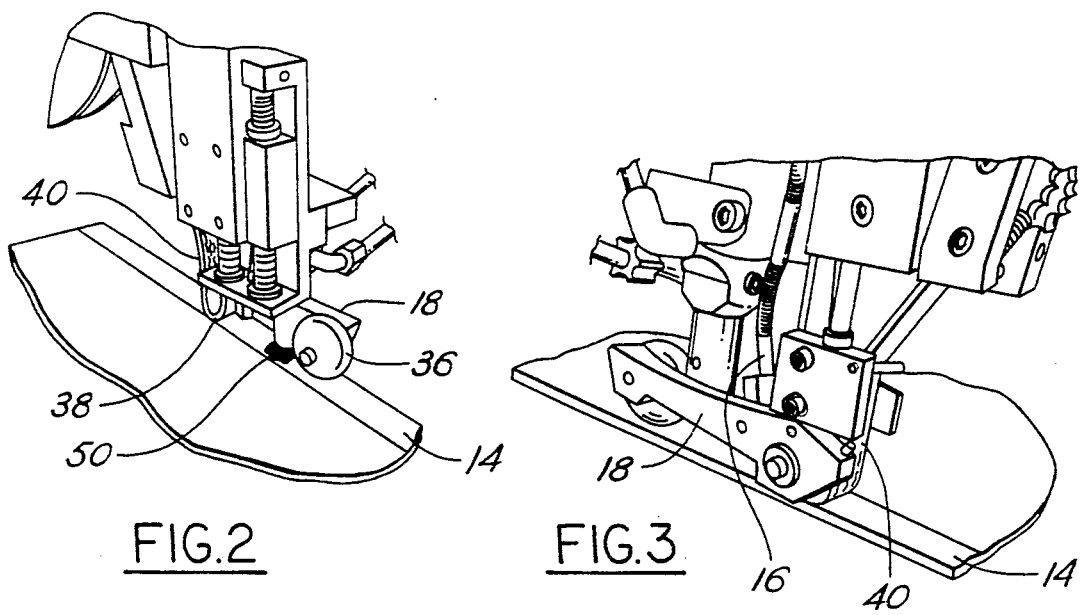
FIG. 2 is an enlarged fragmentary perspective view looking in the direction of arrow 2 of FIG. 1 showing the apparatus engaging the glass surface.
Figure 3:
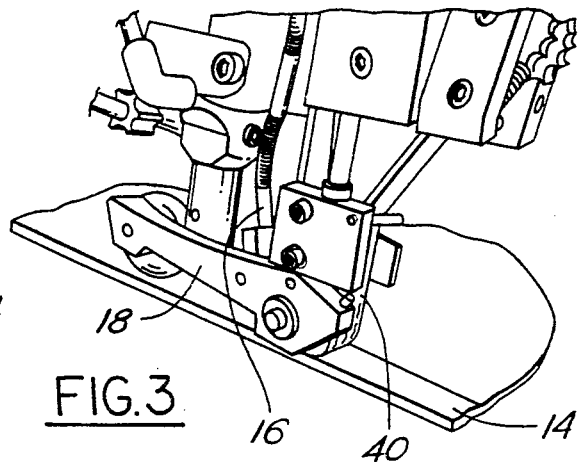
FIG. 3 is an enlarged fragmentary perspective view looking in the direction of arrow 3 of FIG. 1.

The present invention includes an apparatus and a method for detecting the presence or absence of a discontinuity on a glass surface. A description of the preferred embodiment of the apparatus and method follows.

As shown in FIG. 4, an apparatus 12 for detecting the presence of discontinuities on a glass surface 14 includes a transmitting means 16 for directing incident upon and receiving from the glass surface reflected electromagnetic radiation in the infrared range of the spectrum, i.e. 880 nanometers, a positioning means 18 for supporting and positioning transmitting means 16 in a fixed angular and distance relation from the glass surface 14, and a sensing means 20 for sensing the magnitude of the reflected radiation received by the transmitting means 16. Transmitting means 16 is optically connected to the sensing means 20. FIG. 9 shows that a portion of the incident radiation is reflected back to the transmitting means 20 as coincident radiation 15 and a portion scatters as noncoincident radiation 17.

Transmitting means 16 is preferably a commercially available fiber optics light guide such as Model BF-C-36 sold by Tri-Tronics Company, Inc. This particular model has a bundle of fiber optics, approximately half of which transmit and direct emitting radiation towards the glass surface 14 and the other half which receive and transmit reflected radiation from the glass surface 14 or discontinuities 22 located thereon. The emitting and receiving fiber optics are parallel to one another and evenly dispersed throughout the bundle. The bundle of fiber optics is arranged rectangularly and the width of radiation scanning glass surface 14 is approximately 0.55 inch.

Sensing means 20 is a photoelectric sensor such as a Smarteye Switching Model SAL sold by Tri-Tronics Company, Inc. The sensing means 20 is connected to the transmitting means 16 through an Optical Block model F1, also sold by Tri-Tronics Company, Inc. The sensing means 20, i.e. the Smarteye Switching Model SAL, both emits infrared radiation and senses the magnitude of the reflected infrared radiation which is input from the transmitting means 16. It is contemplated that a separate means for generating the infrared light could also be used and connected to the transmitting means 20. The sensing means 20 generates an analog output voltage proportional to the magnitude of reflected radiation input thereto.

Positioning means 18 is a compliance device which adapts to the glass surface 14 and supports and positions the transmitting means 16 in a fixed angular and distance relation relative to the glass surface 14. An angle $\alpha$, as shown in FIG. 4, defines the angle between a line perpendicular to the glass surface 14 and the incident and reflected radiation transmitted through the transmitting means 16 and lies in a plane parallel to a longitudinal member which is also the plane of translation of the apparatus 12. The perpendicular distance between the glass surface 14 and the end of transmitting means 16 is defined by distance $\delta$. $\alpha$ may range from 3° to 18°, and the distance $\delta$ may range from 0.5 to 1.5 inches.

For a particular type of glass surface and fretting (the marginal edge of the glass surface often comes with a black coating or fretting thereon from the glass manufacturer), the optimal angle $\alpha$ and distance $\delta$ are experimentally determined. A variety of $\alpha$ and $\delta$ combinations are investigated to establish which output of voltage from sensing means 20 for reflected radiation received from a dry surface is maximum relative to the output when receiving reflected radiation from a wet surface.

Glass used by different automakers has proven to have different optimal combinations of $\alpha$ and $\delta$. For a particular glass tested, at an $\alpha$ of 15.5 degrees and a $\delta$ of 0.500", the relative difference in reflectivity of the dry surface versus the wet surface has been established to be maximum. The voltage output from the sensing means 20 for a wet surface is nearly zero while with a dry surface a voltage of 15 volts is output. Consequently, the value of voltage output from sensing means 20 is determinative of the presence or absence of the primer coating on glass surface 14. In the event that streaking of the applied primer occurs, the degree of streaking is proportional to the voltage output from sensing means 20 and is somewhat indicative of the amount of liquid or primer present.

As shown in FIG. 4, positioning means 18 includes longitudinal member 30 having a leading end 32 and a trailing end 34. Pivotally connected to the leading end 32 is a rolling member 36 and at the trailing end is a similar pivotally connected rolling member 38, both of which are made of a wear-resistant material such as nylon. The rolling member 38, as shown in FIG. 6, serves as a pulley around which a felt ribbon 40 is driven. The felt ribbon 40 is made of polypropylene and/or polyester material, and is stored on a large rotatable spool 42.

Positioning means 18 further includes a positioning bracket 46 connected to longitudinal member 30 and supports the end of the transmitting means 16. Preferably, the optimal $\alpha$ and $\delta$ for the particular glass surface 14 is experimentally determined as described above, with bracket 46 then being fixedly secured to longitudinal member 30 such that $\alpha$ and $\delta$ are permanently fixed relative to the glass surface 14. This prevents accidental misalignment of $\alpha$ and $\delta$ while apparatus 12 is operating. Alternatively, bracket 46 may be designed such that it is slidably and rotatably adjustable relative to longitudinal member 30 to fix the transmitting means 16 in various angular and distance relations relative to the glass surface 14.

Longitudinal member 30 also supports a dispenser 48 having a brush 50 attached thereto for applying primer. Primer is supplied to the dispenser 48 by a supply tube 52. The brush 50 applies a coating of the primer ahead of the incident and reflected radiation.

A pair of springs 54 provide biasing to ensure that rolling member 36 and felt ribbon 40 maintain contact with the glass surface 14.

The apparatus 12 may be either stationary or moving relative to glass surface 14 when detecting discontinuities 22 on the glass surface 14. Preferably, a robotic linkage 56 supports apparatus 12 such that it is translated about the marginal edge of glass surface 14 with the positioning means 18 having rolling member 36 and the felt ribbon 40 contacting the glass surface 14 while maintaining the relative positioning of transmitting means 16 with respect to glass surface 14. The translational movement of apparatus 12 is such that rolling member 36 will precede felt ribbon 40 across the glass surface 14. The rolling members 36 and 38 are longitudinally spaced rather closely together so that the transmitting means 16 and the brush 50 maintain a relatively uniform distance δ from glass surface 14 as apparatus 12 translates about changing contours of glass surface 14. Using the transmitting and sensing equipment as described above, apparatus 12 may be translated at a rate of 25"/sec while accurately detecting discontinuities 22.

In operation, rolling member 36 and felt ribbon 40 are placed in contact with glass surface 14, with springs 54 biasing the positioning means 18 such that the contours of the glass surface 14 are followed. The positioning bracket 46 is fixedly secured to longitudinal member 30 such that the distance δ and the angle α are permanently set to their desired parameters, which for a glass surface as described above would be preferably at an α of 16.5° and at a δ of 0.500".

The dispenser 48 and associated brush 50 are also positioned such that the brush 50 contacts the glass surface 14.

The sensing means 20 is then calibrated. If there is no interfering discontinuity 22, i.e. a dry or uncracked surface, located on the glass surface 14, a substantial portion of the emitted radiation from transmitting means 16 will reflect off the glass surface 14 and is received by transmitting means 16 which transmits the radiation to sensing means 20. The output of voltage from sensing means 20 is proportional to the magnitude of the reflected radiation and is adjusted such that a steady voltage, i.e. 15 volts, is output in response to emitted infrared radiation upon the clean, continuous glass surface 14. The output voltage relatively to a wetted surface should be very low. FIG. 9 shows schematically that some of incident radiation from transmitting means 20 returns back thereto.

As seen in FIG. 1, robotic linkage 56 supports and translates apparatus 12 about the marginal edge of glass 14. Supply tube 52 supplies dispenser 48 with primer and brush 50 applies a coating of the primer to glass surface 14 as apparatus 12 is translated along the margin of the glass.

When the coating completely covers the glass surface 14, very small amounts of radiation will be reflected back to the transmitting means 20, and accordingly very little voltage will be output from sensing means 20. If no coating is applied, the glass surface will remain fully reflective and a large magnitude of reflected radiation will be received and the 15 volts will be output by sensing means 20. In the event that streaking occurs as shown in FIG. 7, the increase in output voltage will be indicative of the severity of the streaking.

If a sufficiently high voltage is output, i.e. 5.0 volts if the maximum output is 15 volt, a signal device (not shown) may be activated indicating that glass surface 14 is defective and appropriate corrective measures should be taken.

Trailing the applied coating of primer is felt ribbon 40 which wipes and removes the primer from the glass surface 14. The rolling member 38, as shown in FIG. 6, is driven to rotate the felt rope 40 thereabout to ensure that all of the excess primer is removed.

A black primer is applied thereafter, which is a prerequisite to applying a urethane sealant. A pivotally connected trailing rolling member (not shown) similar to rolling member 36 replaces rolling member 38 and is perpendicularly offset from longitudinal member 30 such that the black primer is left undisturbed on surface 14 and is allowed to dry without being crossed by the offset rolling member. The urethane sealant is then applied.

FIG. 8 shows a marginal edge on the glass surface 14 which has a crack therein. The crack serves as a discontinuity 22' which adversely affects reflectivity of glass surface 14 and accordingly creates a spike in the voltage output from sensor means 20. The spike in voltage output may be used to signal that a crack is present in the glass surface and that appropriate corrective measures should again be taken.

While the foregoing specification of this invention has been described in relation to certain preferred embodiments thereof, and many details have been set forth for the purpose of illustration, it will be apparent to those skilled in the art that the invention is susceptible to additional embodiments and that certain of the details described herein can vary considerably without departing from the basic principles of the invention.

What is claimed is:

1. An apparatus for detecting the presence or absence of a discontinuity on a glass surface, the apparatus comprising:
   transmitting means for emitting incident infrared electromagnetic radiation toward the glass surface and for receiving that portion of the infrared electromagnetic radiation reflected from the glass surface which is coincident with the incident radiation;
   positioning means for positioning the transmitting means to direct the incident radiation and coincident portion of the reflected radiation at an angle from a line perpendicular to the glass surface; and
   sensing means optically connected to the transmitting means for sensing the relative magnitude of the coincident portion of the reflected radiation relative to the incident radiation and determining the presence or absence of a discontinuity on the glass surface in accordance therewith.

2. The apparatus of claim 1 wherein the perpendicular distance from the transmitting means to the glass surface is 0.5 to 1.5 inch.

3. The apparatus of claim 2 wherein the angle of the directed radiation is 15.5 degrees and the perpendicular distance is 0.5 inch.

4. The apparatus of claim 1 wherein the means for positioning is a compliance device which includes a longitudinal support member with a front end and a trailing end, each end having mounted thereto a rolling member which translates about the glass surface so as to maintain a relatively fixed angular and distance relationship between the glass surface and the transmitting means.

5. The apparatus of claim 4 wherein the apparatus translates relative to the glass surface while detecting the presence or absence of a discontinuity on the glass surface.

6. The apparatus of claim 4 wherein the means for positioning said transmitting means positions the same to direct the radiation in the plane of translation of the apparatus.

7. The apparatus of claim 1 wherein the discontinuity is a liquid.

8. The apparatus of claim wherein the discontinuity is a crack.

9. The apparatus of claim 1 wherein: the positioning means directs the incident radiation towards the glass surface at an angle of 3-18 degrees form a line perpendicular to the glass surface.

10. A method for detecting the presence or absence of a discontinuity on a glass surface comprising the steps of:
    directing incident infrared electromagnetic radiation towards a glass surface at an angle from a line perpendicular to the glass surface;
    sensing the relative magnitude of that portion of the reflected radiation reflected form the glass surface which is coincident with the incident radiation; and
    determining the presence or absence of a discontinuity on the glass surface in accordance with the relative magnitudes of the incident radiation and the coincident portion oh e reflected radiation.

11. The method of claim 10 wherein the radiation directed and reflected is translated relative to the glass surface so as to sense discontinuities along the glass surface.

12. The method of claim 10 where the discontinuity is a liquid coating.

13. The method of claim 10 where the discontinuity is a crack.

14. The method of claim 10 wherein: the incident radiation is directed towards the glass surface at an angle of 3-18 degrees from a line perpendicular to the glass surface.

* * * * *

UNITED STATES PATENT AND TRADEMARK OFFICE
CERTIFICATE OF CORRECTION

PATENT NO. : 5,144,151

DATED : September 1, 1992

INVENTOR(S) : Brent A. Thorn et al

It is certified that error appears in the above-identified patent and that said Letters Patent is hereby corrected as shown below:

On the title page Item (76), second Inventor name "Brent a. Thorne" should read -- Brent A. Thorn --.

Signed and Sealed this

Sixteenth Day of November, 1993

Attest:

BRUCE LEHMAN

*Attesting Officer*   *Commissioner of Patents and Trademarks*